Figure 1:
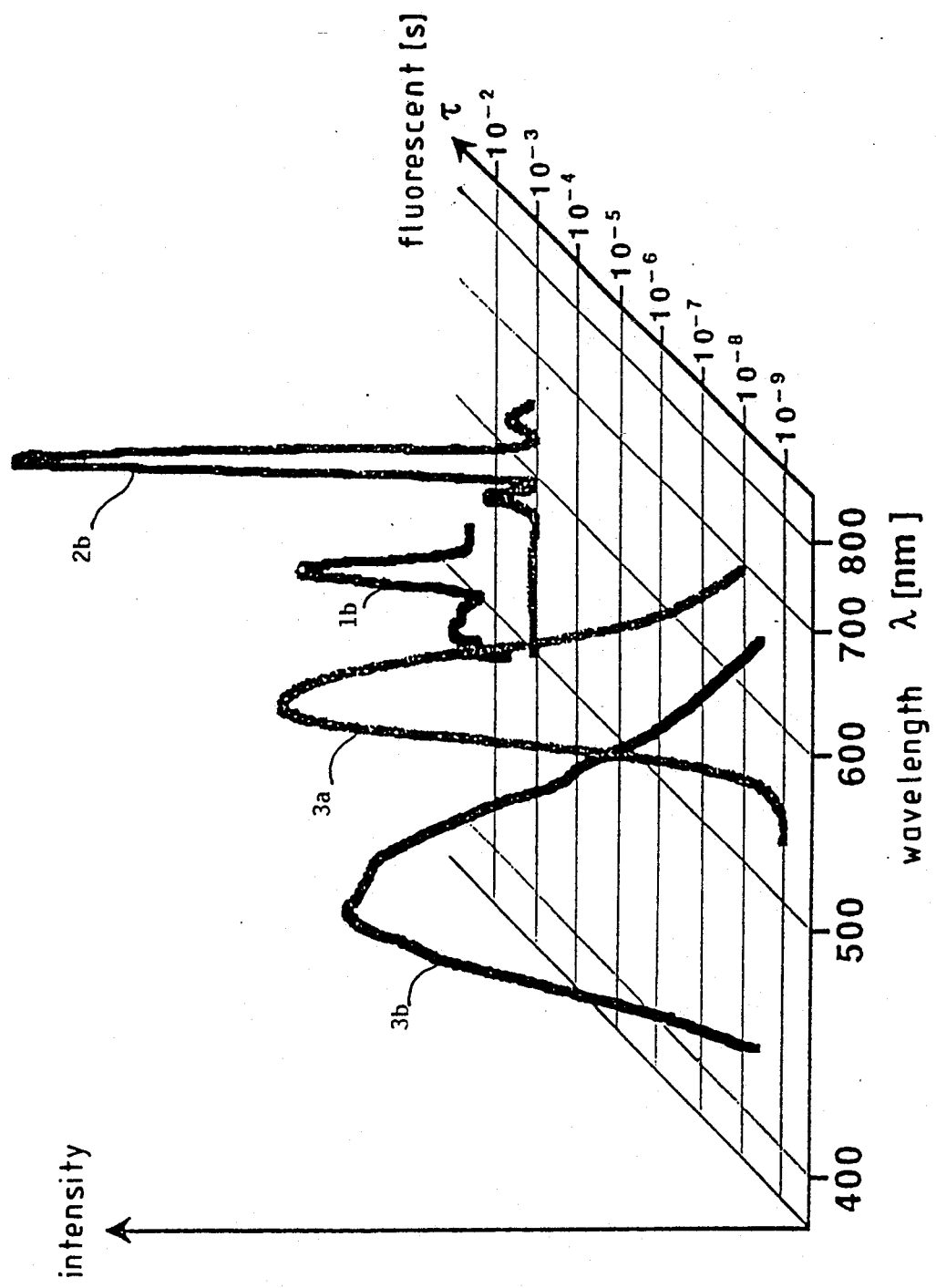

United States Patent [19]
Becker et al.

[11] Patent Number: 5,329,127
[45] Date of Patent: Jul. 12, 1994

[54] METHOD FOR THE IDENTIFICATION OF PLASTICS

[75] Inventors: Arno Becker, Krefeld; Klaus Luttermann, Lohmar; Uwe Claussen, Leverkusen; Peter Orth, Köln; Ludger Heiliger; Aziz E. Sayed, both of Leverkusen, all of Fed. Rep. of Germany

[73] Assignee: Bayer AG, Leverkusen, Fed. Rep. of Germany

[21] Appl. No.: 44,731

[22] Filed: Apr. 12, 1993

[30] Foreign Application Priority Data

Apr. 23, 1992 [DE] Fed. Rep. of Germany ....... 4213323

[51] Int. Cl.$^5$ .......................... G01N 21/64; C08J 3/20
[52] U.S. Cl. .................. 250/459.1; 250/302; 235/491
[58] Field of Search .................. 250/302, 458.1, 459.1; 235/491

[56] References Cited

U.S. PATENT DOCUMENTS

| | | | |
|---|---|---|---|
| 3,530,075 | 9/1970 | Wiebe | 252/300 |
| 3,772,099 | 11/1973 | Ryan et al. | 250/302 X |
| 4,238,524 | 12/1980 | LaLiberte et al. | 427/7 |
| 5,005,873 | 4/1991 | West | 235/491 X |
| 5,201,921 | 4/1993 | Luttermann et al. | 209/576 X |

FOREIGN PATENT DOCUMENTS

| | | |
|---|---|---|
| 0476416 | 3/1992 | European Pat. Off. . |
| 0506999 | 10/1992 | European Pat. Off. . |
| 4029167 | 3/1992 | Fed. Rep. of Germany . |
| 2095822 | 10/1982 | United Kingdom ........... 235/491 |

Primary Examiner—Constantine Hannaher
Assistant Examiner—Edward J. Glick
Attorney, Agent, or Firm—Connolly & Hutz

[57] ABSTRACT

A method of identifying different plastics, wherein each plastic is provided with a plurality of fluorescent dyes which differ in terms of their emission frequencies and-/or in terms of the duration of their fluorescence, so that a fluorescence pattern, which is distinguished by the duration of the fluorescence and/or by the frequencies occurring, can unambiguously be assigned to each plastic.

14 Claims, 1 Drawing Sheet

METHOD FOR THE IDENTIFICATION OF PLASTICS

DE-OS 40 29 167 describes a process for the identification of plastics, in which a small amount of a fluorescent dye is added to the plastic during or after its manufacture. In principle, a plastic treated in this way can be irradiated with UV light and can be identified again by examining the fluorescent radiation. One difficulty with this type of identification is that the amount of suitable fluorescent dyes is limited. Moreover, in order to be able to separate different plastics labelled with different fluorescent dyes, it must be ensured that the fluorescence spectra are sufficiently clearly different from each other.

Since it is important in the re-use of plastics to produce pure grades of material for recycling, a large number of fluorescent dyes which can be unambiguously distinguished from each other are required as "markers" for plastics.

It has been found that not only can fluorescent dyes with different fluorescence spectra be admixed with plastics in order to distinguish the latter from each other, but also that the duration of the fluorescence can be utilized in addition. Namely, there are fluorescent dyes which cannot be distinguished on the basis of their spectra, but which differ very markedly in terms of the duration of their fluorescence.

Accordingly, the present invention relates to a method for the identification of different plastics, which is characterised in that each plastic is provided with a plurality of fluorescent dyes which differ in terms of their emission frequencies and/or the duration of their fluorescence, so that a fluorescence pattern, which is distinguished by the duration of the fluorescence and/or by the frequencies occurring, can be unambiguously assigned to each plastic.

This process will be described below by means of an example. The example employed two of the fluorescent dyes from DE-OS 40 29 167 (for example, dyes No. 1 and No. 4 of the embodiment exemplified)—hereinafter called fluorescent dyes—and two complex salts of rare earth metals, namely a complex salt of terbium and a complex salt of europium. The terbium salt had a green fluorescence, just like the green fluorescent dye, and the europium salt had a red florescence, just like the red fluorescent dye. However, the fluorescent dyes exhibited of fluorescence with a duration in the nanosecond region, whilst that of the complexes of the rare earth metals was in the region of a few hundred microseconds. When a sample of plastic, which contained one of the two dyes and a complex of a rare earth metal, was excited by means of a short photoflash with a duration of 1 nanosecond, for example, the fluorescence of the fluorescent dye had decayed almost completely after 1000 nanoseconds, whilst the fluorescence lifetime of the metal complex was sustained for about 500 microseconds. On the other hand, the fluorescence of the material exhibiting long-term fluorescence made practically no contribution to the total intensity of the fluorescence during the first 10 nanoseconds, because the intensity of the short-lived fluorescence was greater by a factor of about 50,000 in that period. By monitoring the fluorescence behavior over a period of time, it can therefore easily be determined whether a plastic contains one or other or both marker materials, even if the fluorescence spectra are not significantly different. If two materials with a green fluorescence and two materials with a red fluorescence are available, as provided above, fifteen different combinations can be formed therefrom, i.e. fifteen different plastics can be labelled using only these four marker materials so that they can be unambiguously re-identified. When carrying out the process in practice the marker substances can be incorporated in polymers which are miscible with the polymers to be identified and added in this form.

EXAMPLE 1

Preparation of a polymeric terbium complex 1a) 0.05 mole p-aminosalicylic acid was heated with 0.05 mole m-TMI © ($\alpha,\alpha$-dimethyl-m-isopropenylbenzyl isocyanate) and an amount of 2,6-bis-$^t$butylphenol sufficient to cover the tip of a spatula in 100 ml dry acetone for 6 hours under reflux. The precipitate formed was filtered off under suction, subsequently washed with cold acetone and dried. $^1$H NMR and IR analyses showed the presence of the expected disubstituted urea as a pure product ($\gamma$ $^1$H 6.7 and 8.8 ppm, $\omega_{C-H}$urea=1630 cm$^{-1}$). Yield: about 63% theoretical.

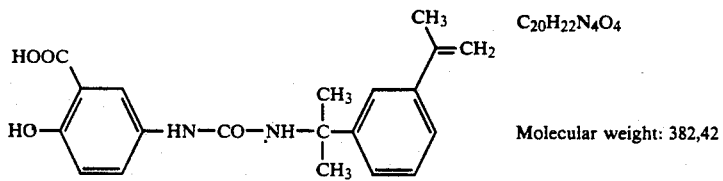

$C_{20}H_{22}N_4O_4$

Molecular weight: 382,42

1b) 0.25 g Tb(NO$_3$)$_3$.5H$_2$O (51% Tb), 1.02 g of product 1a) and 0.45 g dimethylaminoethyl methacrylate were dissolved in 54.9 ml dimethyl acetamide and complex formation was checked by UV excitation at 366 nm.

1.72 g ethylene glycol dimethacrylate, 3.7 g stearyl methacrylate and 0.17 g azobis-isobutyronitrile were added, and polymerisation was effected at 65° C. for 16 hours. After filtering off the precipitate under suction and washing with methanol, the filtered product was transferred into methanol, filtered off under suction, and then washed and dried. Yield: 89% theoretical. A copolymer was obtained containing the complexed terbium, which exhibited an intense green fluorescence after UV excitation. The final product contained 1.8% Tb.

EXAMPLE 2

Preparation of a polymeric europium complex 2a) 0.05 mole 1-(2-naphthoyl)-3,3,3-trifluoroacetone was dissolved in 50 ml methanol. 0.05 mole sodium methanolate from a 30 weight % solution of sodium methanolate in methanol was then slowly added at 0° C., the reaction mixture was heated to room temperature, 0.05 ml chloromethyl styrene was added and the mixture was heated for 16 hours under reflux. The fine precipitate (NaCl) produced was filtered off, the solution was reduced to about ⅓ of its initial volume under the vacuum from a water pump and then treated with an amount of water sufficient just to dissolve the precipitate formed. The organic phase was separated off, the aqueous phase was shaken twice with chloroform, and the purified organic phase was dried over sodium sulphate, filtered and evaporated. The crude product was purified over silica gel (0.063–0.2 mm) in a solvent mixture comprising toluene:methylene chloride:ethyl acetate:methanol in a ratio of 5:3:1:0.5 ($\gamma$ $^{19}$F-76.6 ppm; yield: about 25% theoretical).

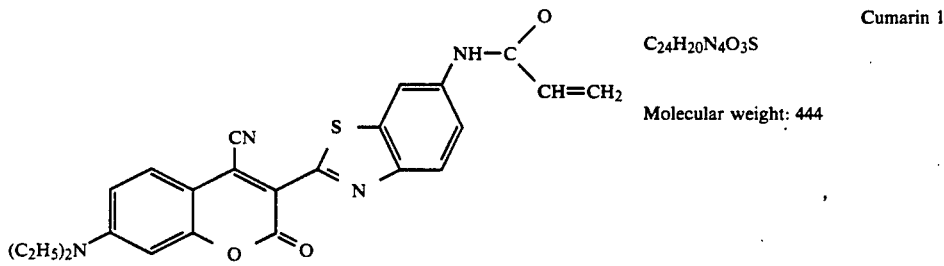

2b) 0.25 g EuCl$_3$.6H$_2$O (41% Eu≅0.1 g), 2.11 g product 2a) and 0.86 g dimethylaminoethyl methacrylate were dissolved in 135.5 ml methanol and complex formation was checked by UV excitation at 366 nm (strong red fluorescence). 3.57 g ethylene glycol dimethacrylate, 28.5 g stearyl methacrylate and 0.35 g azoisobutyronitrile were then added, and the apparatus was evacuated and flushed with pure nitrogen. Evacuation and flushing were repeated twice more, and the mixture was heated to 65° C. A white precipitate was visible after only a few hours; precipitation was complete after a reaction time of 16 hours. The precipitate was filtered off under suction, and then washed with methanol and dried. Yield: 90% theoretical. A copolymer was obtained which contained the complexed europium and which exhibited an intense red fluorescence under UV excitation.

The final product contained 0.3% Eu.

EXAMPLE 3

Polymeric fluorescent dyes 3a) 0.25 g cumarin 1

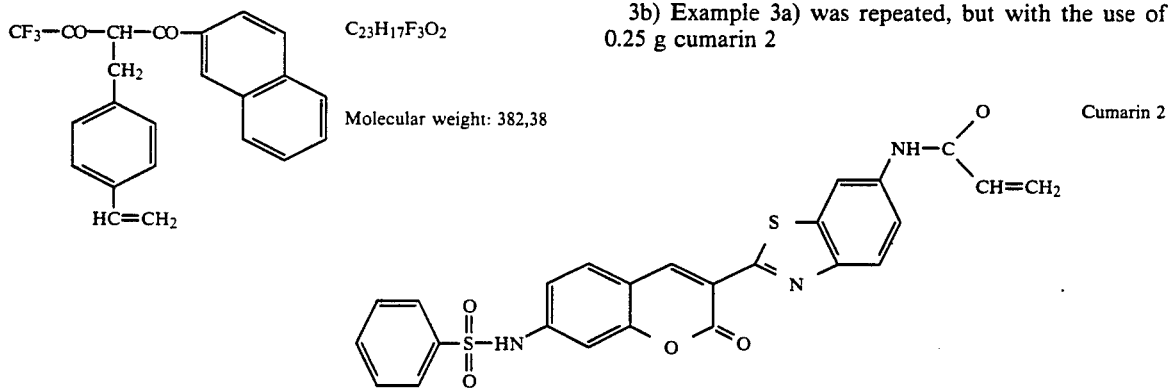

1 g methyl methacrylate and 8.25 g stearyl methacrylate were dissolved in 30 ml dimethyl acetamide and heated to 65° C. After adding 0.1 g azobisisobutyronitrile, the mixture was stirred for 16 hours at this temperature. The precipitate was filtered off under suction, dissolved in methylene chloride, reprecipitated in isopropanol and dried. Yield: 69% theoretical, comprising a copolymer containing the dye cumarin 1 which exhibited a red fluorescence on excitation with UV light.

3b) Example 3a) was repeated, but with the use of 0.25 g cumarin 2

Yield: 70% theoretical, comprising a copolymer containing the dye cumarin 2 which exhibited a green fluorescence on excitation with UV light.

EXAMPLE 4

Incorporation of polymers 1b, 2b, 3a and 3b in polyethylene

A Haake rheometer kneader with a volumetric capacity of 50 ml was heated to 130° C. and 44 g granular polyethylene (LDPE, Novex Exp. 2184) was spread inside. After kneading for 10 minutes, 0.37 g 2b), 0.04 g each of 3a) and 3b), and 0.185 g 1b) were added and kneaded for a further 15 minutes at this temperature. The polymer thus contained about 1–8% of each of these compounds. The complex compounds 1b) and 2b) exhibited a green and red fluorescence, respectively, which lasted for about 500 microseconds. The dyes 3a) and 3b) exhibited a red and green fluorescence, respectively, with a duration of a few nanoseconds.

The relationships are illustrated in FIG. 1 which shows the fluorescence spectra and fluorescence time of the four materials described in Examples 1–3 as tested in Example 4.

EXAMPLE 5

Detection of the fluorescence signals from a sample produced as in Example 4

Separation of the fluorescence signals was effected using an FL 900 time-resolution fluorescence spectrometer manufactured by Edinburgh Instruments.

A sample prepared as in Example 4 was excited by means of a microsecond photoflash lamp and the fluorescence decay curves were determined in channels with a spectral width of 2 nm over the wavelength interval from 450 nm to 640 nm. Discrimination with respect to time was effected using appropriate software:

For example, the integration of each channel over the first 20 microseconds gave the spectra of components 3a) and 3b) with the short-lived fluorescence. Commencing integration at 80 microseconds and integrating over 1 millisecond gave the contribution to the signal from the complex compounds 1b) and 2b).

Discrimination with regard to the emission frequency was obtained directly from the spectra, since the emissions did not overlap significantly.

Measurement of the said discriminations could be simplified considerably by the determination of defined time or frequency windows.

We claim:

1. A method of identifying different plastics comprising the following steps:
   a) providing each plastic with a plurality of fluorescent marker materials wherein said plurality of fluorescent marker materials contains at least one marker material that has a duration of fluorescence which differs from the duration of fluorescence of the other marker materials and further wherein each plastic is provided with a different combination of said fluorescent marker materials;
   b) exposing the plastics to a source of radiation which will cause the marker materials to fluoresce;
   c) measuring the fluorescence patterns of the plastics after exposure to the radiation in step b); and
   d) identifying each plastic by the different durations of fluorescence exhibited in the fluorescence patterns measured in step c).

2. The method of claim 1, wherein said fluorescent marker materials include a complex salt of a rare earth metal.

3. The method of claim 2, wherein said rare earth metal is terbium or europium.

4. The method of claim 1, wherein said fluorescent marker materials include a fluorescent dye.

5. The method of claim 1, wherein said fluorescent marker materials include a complex salt of a rare earth metal and a fluorescent dye.

6. The method of claim 1, wherein said fluorescent marker materials are incorporated into polymers which are miscible with the plastics before said marker materials are added to the plastics.

7. The method of claim 1, wherein the radiation is UV radiation.

8. A method of identifying different plastics comprising the following steps:
   a) providing each plastic with a plurality of fluorescent marker materials wherein said plurality of fluorescent marker materials contains (i) at least one marker material that has a duration of fluorescence which differs from the duration of fluorescence of the other marker materials and (ii) at least one marker material that has an emission frequency that is different from the emission frequency or frequencies of the other marker materials, and further wherein each plastic is provided with a different combination of said fluorescent marker materials;
   b) exposing the plastics to a source of radiation which will cause the marker materials to fluoresce;
   c) measuring the fluorescence patterns of the plastics after exposure to the radiation in step b); and
   d) identifying each plastic by the different durations of fluorescence in combination with the different emission frequencies exhibited in the fluorescence patterns measured in step c).

9. The method of claim 8, wherein said fluorescent marker materials include a complex salt of a rare earth metal.

10. The method of claim 9, wherein said rare earth metal is terbium or europium.

11. The method of claim 8, wherein said fluorescent marker materials include a fluorescent dye.

12. The method of claim 8, wherein said fluorescent marker materials include a complex salt of a rare earth metal and a fluorescent dye.

13. The method of claim 8, wherein said fluorescent marker materials are incorporated into polymers which are miscible with the plastics before said marker materials are added to the plastics.

14. The method of claim 8, wherein the radiation is UV radiation.

* * * * *